(12) United States Patent
Smith (10) Patent No.: US 6,176,597 B1
(45) Date of Patent: Jan. 23, 2001

(54) REFLECTOR FOR SURGICAL LIGHT APPARATUS

(75) Inventor: A. Michael Smith, Boulder, CO (US)

(73) Assignee: Hill-Rom, Inc., Batesville, IN (US)

( * ) Notice: Under 35 U.S.C. 154(b), the term of this patent shall be extended for 0 days.

(21) Appl. No.: 09/050,265

(22) Filed: Mar. 30, 1998

Related U.S. Application Data
(60) Provisional application No. 60/079,667, filed on Mar. 27, 1998.

(51) Int. Cl.$^7$ .................................................... F21V 7/09
(52) U.S. Cl. ............................ 362/297; 362/346; 362/804
(58) Field of Search .................................. 362/297, 346, 362/804, 304, 348, 293

(56) References Cited

U.S. PATENT DOCUMENTS

| | | |
|---|---|---|
| 2,114,664 | 4/1938 | Gelb . |
| 2,173,325 | 9/1939 | Alexander . |
| 2,297,781 | 10/1942 | Korengold . |
| 3,511,983 | 5/1970 | Dorman . |
| 3,662,165 | 5/1972 | Osteen et al. . |
| 3,666,939 | 5/1972 | Ota . |
| 3,700,883 | 10/1972 | Donohue et al. . |
| 3,702,928 | 11/1972 | Alger . |
| 3,826,913 | 7/1974 | Downing et al. . |
| 3,928,757 | 12/1975 | Nelson . |

(List continued on next page.)

FOREIGN PATENT DOCUMENTS

| | | |
|---|---|---|
| 35 06 030 | 8/1986 | (DE) . |
| 4140 325 | 5/1993 | (DE) . |
| 0 091 797 | 10/1983 | (EP) . |
| 0 774 619 A1 | 5/1997 | (EP) . |
| 877546 | 9/1961 | (GB) . |
| 927676 | 5/1963 | (GB) . |

OTHER PUBLICATIONS

Berchtold Corporation, "Chromophare® C–571 Superior lighting technology is the secret of our success", Feb. 1995, 8 pages.

Berchtold Corporation, Chromophare® C–570 Service Manual, date unknown, 20 pages.

Primary Examiner—Thomas M. Sember
(74) Attorney, Agent, or Firm—Barnes & Thornburg (57) ABSTRACT

A surgical lighthead includes a light source having a reference point defined thereon and a reflector including a concave reflector surface which has a central axis. The concave reflector surface is formed to include a plurality of facets configured to reflect light emanating from the light source. The plurality of facets includes a first set of facets for which each associated longitudinal boundary line is angularly spaced by a first angle from each of the next adjacent boundary lines relative to the central axis. In addition, the plurality of facets includes a second set of facets for which each associated longitudinal boundary line is angularly spaced by a second angle from each of the next adjacent boundary lines relative to the central axis.

26 Claims, 6 Drawing Sheets

U.S. PATENT DOCUMENTS

| | | |
|---|---|---|
| 4,021,659 | 5/1977 | Wiley . |
| 4,037,096 | 7/1977 | Brendgord et al. . |
| 4,149,227 | 4/1979 | Dorman . |
| 4,153,929 | 5/1979 | Laudenschlarger et al. . |
| 4,234,247 | 11/1980 | Dorman . |
| 4,242,727 | 12/1980 | de Vos et al. . |
| 4,254,455 | 3/1981 | Neal, Jr. . |
| 4,288,844 | 9/1981 | Fisher et al. . |
| 4,617,619 | 10/1986 | Gehly . |
| 4,799,136 | 1/1989 | Molnar . |
| 4,837,668 | 6/1989 | Koehler . |
| 4,855,886 | 8/1989 | Eijkelenboom et al. . |
| 4,937,715 | 6/1990 | O'Shea et al. . |
| 4,994,945 | 2/1991 | O'Shea et al. . |
| 5,001,616 | 3/1991 | Gehly et al. . |
| 5,037,191 | 8/1991 | Cheng . |
| 5,038,254 | 8/1991 | Fabbri et al. . |
| 5,093,769 | 3/1992 | Luntsford . |
| 5,165,786 | 11/1992 | Hubert . |
| 5,178,452 | 1/1993 | Scholz . |
| 5,199,785 | 4/1993 | Scholz . |
| 5,235,470 | 8/1993 | Cheng . |
| 5,295,052 | 3/1994 | Chin et al. . |
| 5,331,530 | 7/1994 | Scholz . |
| 5,347,431 | 9/1994 | Blackwell et al. . |
| 5,383,105 | 1/1995 | Agut . |
| 5,483,430 | 1/1996 | Stapel et al. . |
| 5,485,319 | 1/1996 | Lemons . |
| 5,539,626 | 7/1996 | Scholz . |
| 5,544,030 * | 8/1996 | Wijbenga ............................. 362/346 |
| 5,568,967 | 10/1996 | Sikkens et al. . |

* cited by examiner

REFLECTOR FOR SURGICAL LIGHT APPARATUS

This case claims priority benefits to provisional application No. 60/079,667 filed on Mar. 27, 1998.

BACKGROUND AND SUMMARY OF THE INVENTION

The present invention relates to a surgical light apparatus, and particularly, to a reflector for a surgical light apparatus. More particularly, the present invention relates to a surgical light reflector having a concave reflector surface for reflecting light onto a surgical site.

Surgical lights used in hospital operating rooms to illuminate surgical sites on patients are known. Many surgical lights are suspended from a ceiling of a hospital room by arm mechanisms which are movable to permit adjustment of the location of the surgical light relative to the patient. It is common for surgical lights to be placed in a position behind a surgeon such that the surgeon's head is located between the surgical light and the surgical site. Surgical lights having a dome-shaped reflector to reflect light toward the surgical site around the head of the surgeon are known. It is desirable for surgical lights to provide a high illuminance level, to shine light deeply into a patient's body cavity, and to resist shadowing caused by interference from personnel and instruments.

According to the present invention, a surgical lighthead includes a light source having a reference point defined thereon and a reflector including a concave reflector surface which has a central axis. The concave reflector surface is formed to include a plurality of facets configured to reflect light emanating from the light source. Each facet extends between an associated pair of longitudinal boundary lines and an associated pair of latitudinal boundary lines. The plurality of facets includes a first set of facets for which each associated longitudinal boundary line is angularly spaced by a first angle from each of the next adjacent boundary lines relative to the central axis. In addition, the plurality of facets includes a second set of facets for which each associated longitudinal boundary line is angularly spaced by a second angle from each of the next adjacent boundary lines relative to the central axis.

In preferred embodiments, the first latitudinal boundary lines are angularly spaced relative to the reference point by a different amount than the second latitudinal boundary lines are angularly spaced relative to the reference point. The first set of facets are arranged so as to contribute primarily to shadow reduction performance of the surgical lighthead and the second set of facets are arranged to contribute primarily to pattern size performance of the surgical lighthead.

Additional features and advantages of the present invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
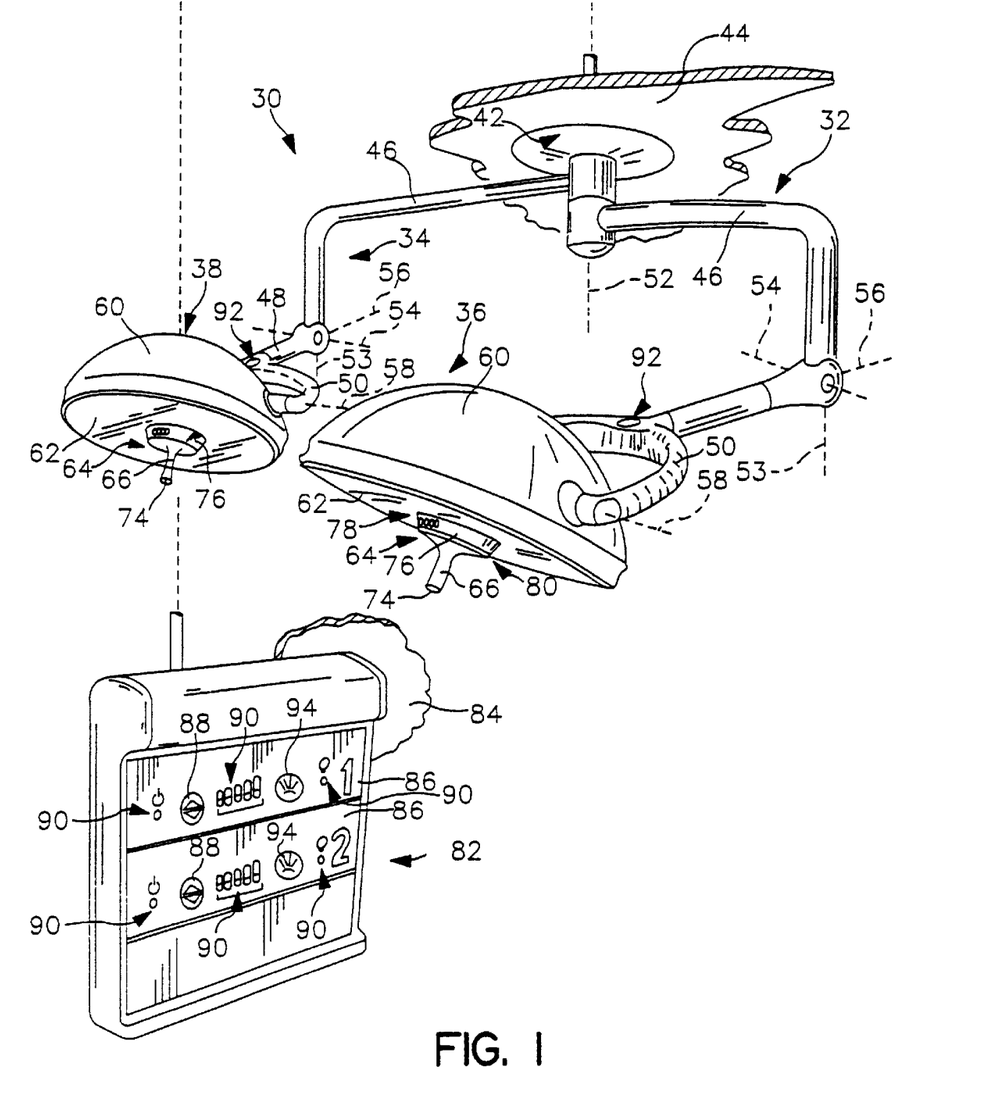
FIG. 1 is an isometric view of a surgical light apparatus in accordance with the present invention showing a first surgical lighthead suspended from a ceiling of a hospital room by a first arm assembly, a second surgical lighthead suspended from the ceiling of the hospital room by a second arm assembly, and a light-controller box mounted to a wall of the hospital room.

A surgical light apparatus 30 includes a first arm assembly 32, a second arm assembly 34, a first lighthead 36 coupled to first arm assembly 32, and a second lighthead 38 coupled to second arm assembly 34 as shown in FIG. 1. First and second arm assemblies 32, 34 each couple to a common mounting apparatus 42 which is configured to mount to suitable support structure (not shown) associated with a ceiling 44. Each arm assembly 32, 34 includes an L-shaped upper arm 46, a lower arm 48, and a yoke 50. Each upper arm 46 is independently pivotable relative to mounting apparatus 42 about a vertical pivot axis 52. Each lower arm 48 is pivotable relative to the respective upper arm 46 about a respective horizontal pivot axis 54 and about a respective vertical pivot axis 53 that is spaced from pivot axis 52. In addition, each yoke 50 is pivotable relative to the respective lower arm 48 about a respective pivot axis 56 and each of lightheads 36, 38 is pivotable relative to the respective yoke 50 about a respective pivot axis 58. Thus, arm assemblies 32, 34 and lightheads 36, 38 are movable to a variety of positions relative to ceiling 44.

Figure 2:
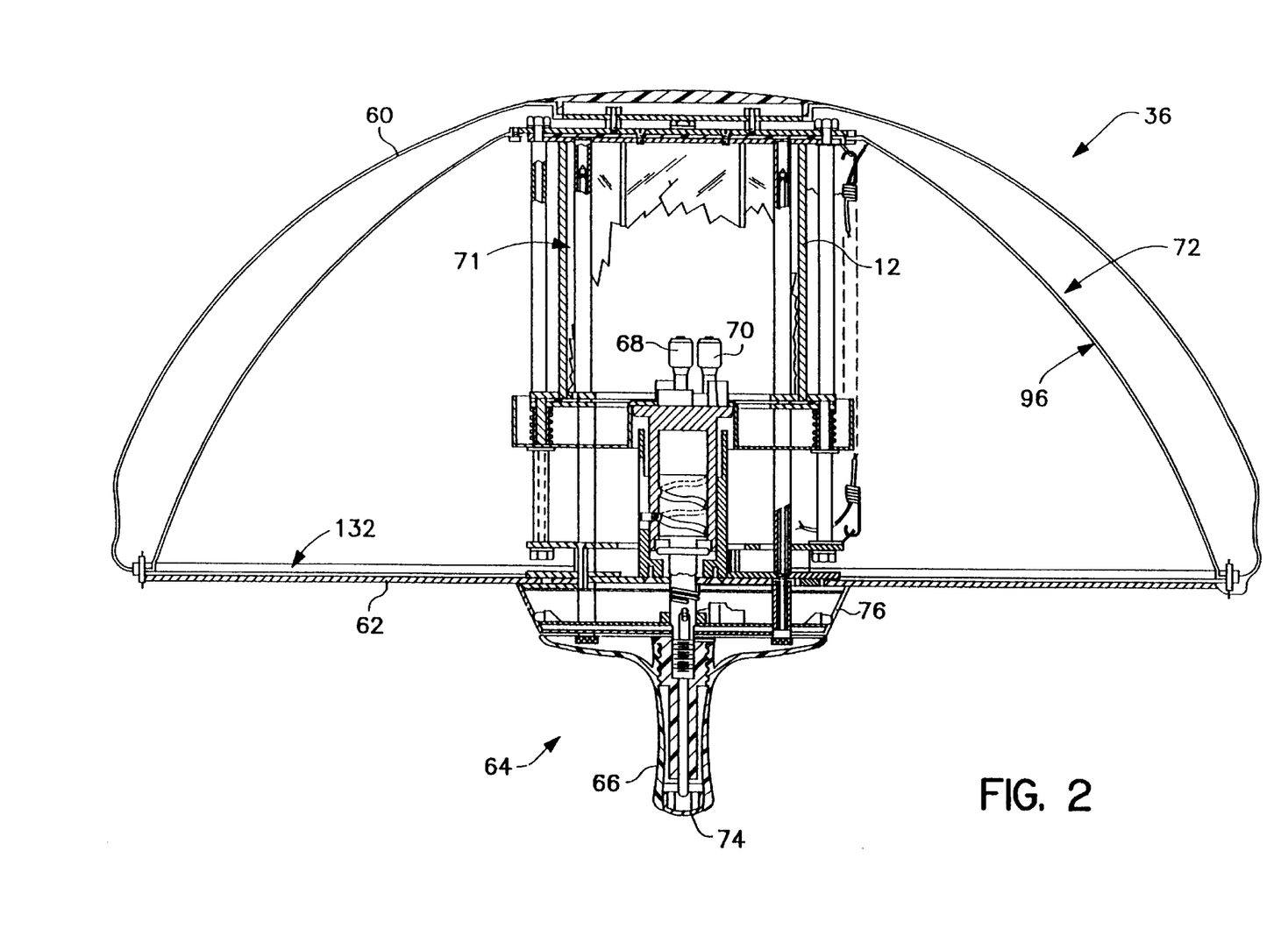
FIG. 2 is a sectional view of the first surgical lighthead of FIG. 1, taken along line 2—2, showing a dome-shaped outer cover, a dome-shaped reflector surrounded by the outer cover, a lamp assembly surrounded by the reflector, and a handle assembly coupled to the lamp assembly.

Each lighthead 36, 38 includes a dome-shaped housing 60, a lens 62 through which light shines from the respective lighthead 36, 38, and a handle assembly 64 as shown in FIG. 1. Each handle assembly 64 includes a handle 66 which is grasped by a surgeon to move the respective lighthead 36, 38 and associated arm assembly 32, 34 to a desired position. Each lighthead 36, 38 includes a main light bulb 68 and a redundant light bulb 70 as shown in FIG. 2 with reference to surgical lighthead 36. In addition, each lighthead 36, 38 includes a reflector 72 that reflects light emanating from either bulb 68 or bulb 70 to illuminate a surgical site on a patient. Redundant bulb 70 remains in an off state until main light bulb 68 burns out and then redundant bulb 70 turns on automatically. Thus, only one of bulbs 68, 70 is on at any instance in time when surgical light apparatus 30 is in use. Each lighthead 36, 38 also includes a light absorption filter 71 as shown in FIG. 2 with reference to surgical lighthead 36. Light absorption filter 71 is fabricated from specially formulated glass which filters most of the near and intermediate infra-red emissions from either of bulbs 68, 70.

The description below of lighthead 36 and the operation of lighthead 36 applies as well to lighthead 38 and the operation of lighthead 38 unless specifically noted otherwise. In addition, although surgical light apparatus 30 includes two arm assemblies 32, 34 and two lightheads 36, 38 as shown in FIG. 1, it is within the scope of the invention as presently perceived for a different number of arm assemblies and corresponding lightheads to be provided. For example, a surgical light apparatus having only one arm assembly and one corresponding lighthead and a surgical light apparatus having three or more arm assemblies and three or more corresponding lightheads are possible.

Handle 66 of each handle assembly 64 is rotatable to move main light bulb 68 and redundant light bulb 70 relative to reflector 72 to adjust the pattern size of reflected light that illuminates the surgical site. The pattern size may be thought of generally as the diameter of the area illuminated by the associated lighthead 36, 38. In addition, handle assembly 64 includes a button 74 at the bottom of handle 66 which is pressed to adjust the intensity level at which light emanates from bulbs 68, 70. Handle assembly 64 includes an escutcheon 76 above handle 66. Handle assembly 64 further includes a first set of LED's 78 and a second set of LED's 80 that are visible on respective sides of escutcheon 76 to provide user information regarding whether one of bulbs 68, 70 is in use or in a standby mode, whether redundant bulb 70 or main bulb 68 is the operative bulb, and the intensity level at which light is emanating from the operative one of bulbs 68, 70. In preferred embodiments, bulbs 68, 70 are each tungsten halogen lamps.

Surgical light apparatus 30 includes a controller box 82, shown in FIG. 1, which is mounted to a wall 84 or other suitable structure and which is coupled electrically to surgical lightheads 36, 38 to control the operation of bulbs 68, 70. Controller box 82 includes a control panel 86 having buttons 88 and sets of LED's 90 that are associated with each respective lighthead 36, 38. Each set of LED's 90 are arranged similarly and provide the same information as LED's 78, 80 of the respective lighthead 36, 38. In addition, each button 88 is pressed to change the light intensity of respective bulbs 68, 70 in the same manner that button 74 of the associated lighthead 36, 38 is pressed to change the light intensity of bulbs 68, 70. Thus, the operation of bulbs 68, 70 is controllable either with the respective handle assembly 64 or controller box 82. Surgical light apparatus 30 optionally may include a task light 92, shown in FIG. 1, and controller box 82 optionally may include a button 94 that is pressed to turn task light 92 on and off.

Other features of surgical light apparatus 30 are discussed and shown in detail in co-pending patent applications Ser. No. 09/050,530 now U.S. Pat. No. 6,012,821 (entitled Support Arm for Surgical Light Apparatus); Ser. No. 09/050,529 (entitled Surgical Light Apparatus with Improved Cooling); Ser. No. 29/085,726 entitled Surgical Light Apparatus); Ser. No. 09/050,543 (entitled Controls for Surgical Light Apparatus); Ser. No. 09/050,576 (entitled Task Light for Surgical Light Apparatus); Ser. No. 29/085,751 now Design Pat. No. B421,148 (entitled Handle for Surgical Lighthead); and Ser. No. 29/085,727 now Design Pat. No. D421,507 (entitled Surgical Lighthead Cover) filed concurrently herewith, all of which are hereby incorporated by reference herein.

Figure 3:
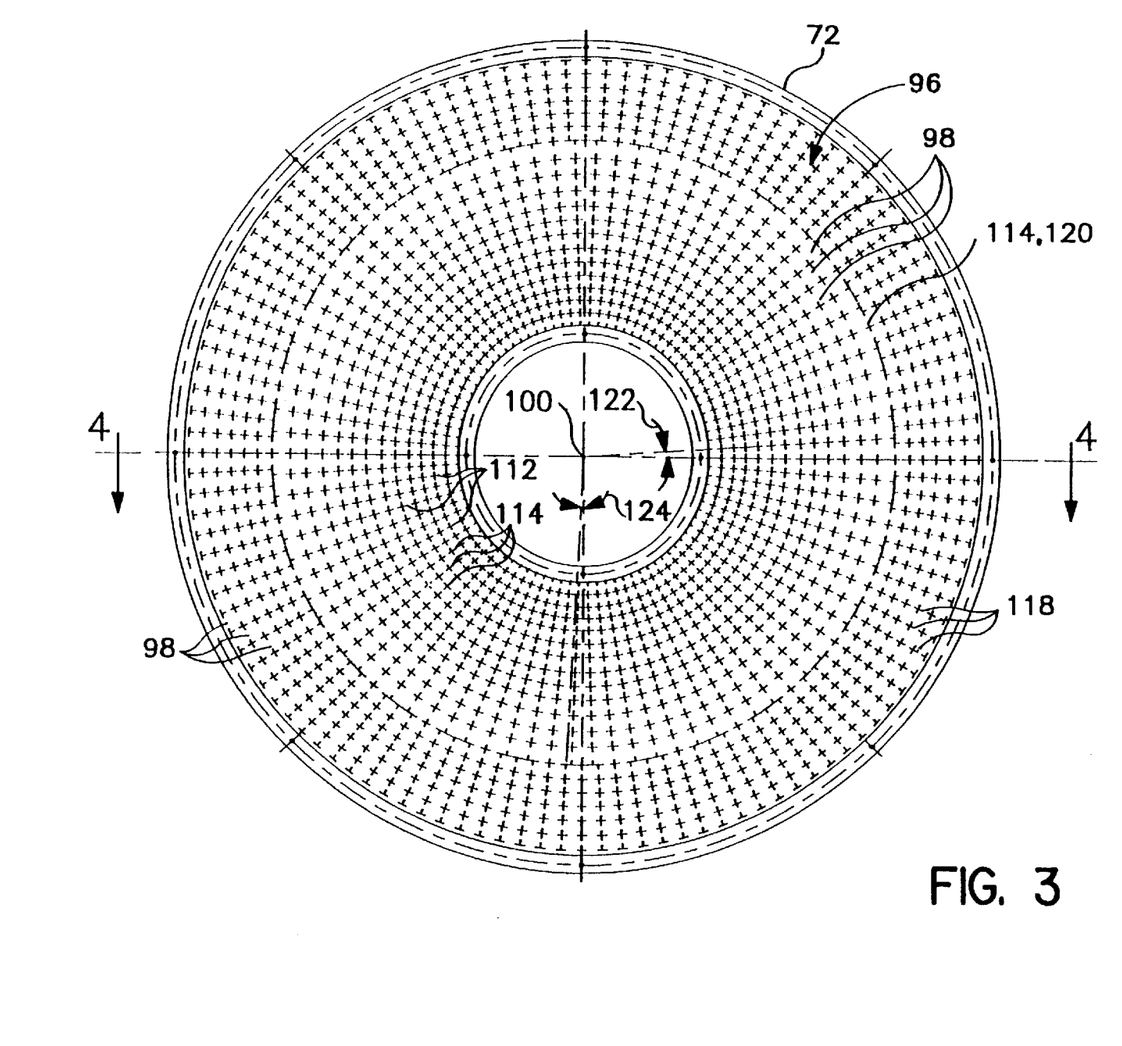
FIG. 3 is a bottom plan view of the reflector of FIG. 2 showing that a concave reflector surface of the reflector is formed to include a plurality of facets, each facet extending between an associated pair of longitudinal boundary lines and a pair of latitudinal boundary lines, the plurality of facets including a first set of facets having thirteen annular courses of facets, and the plurality of facets including a second set of facets having six annular courses of facets.
Figure 4:
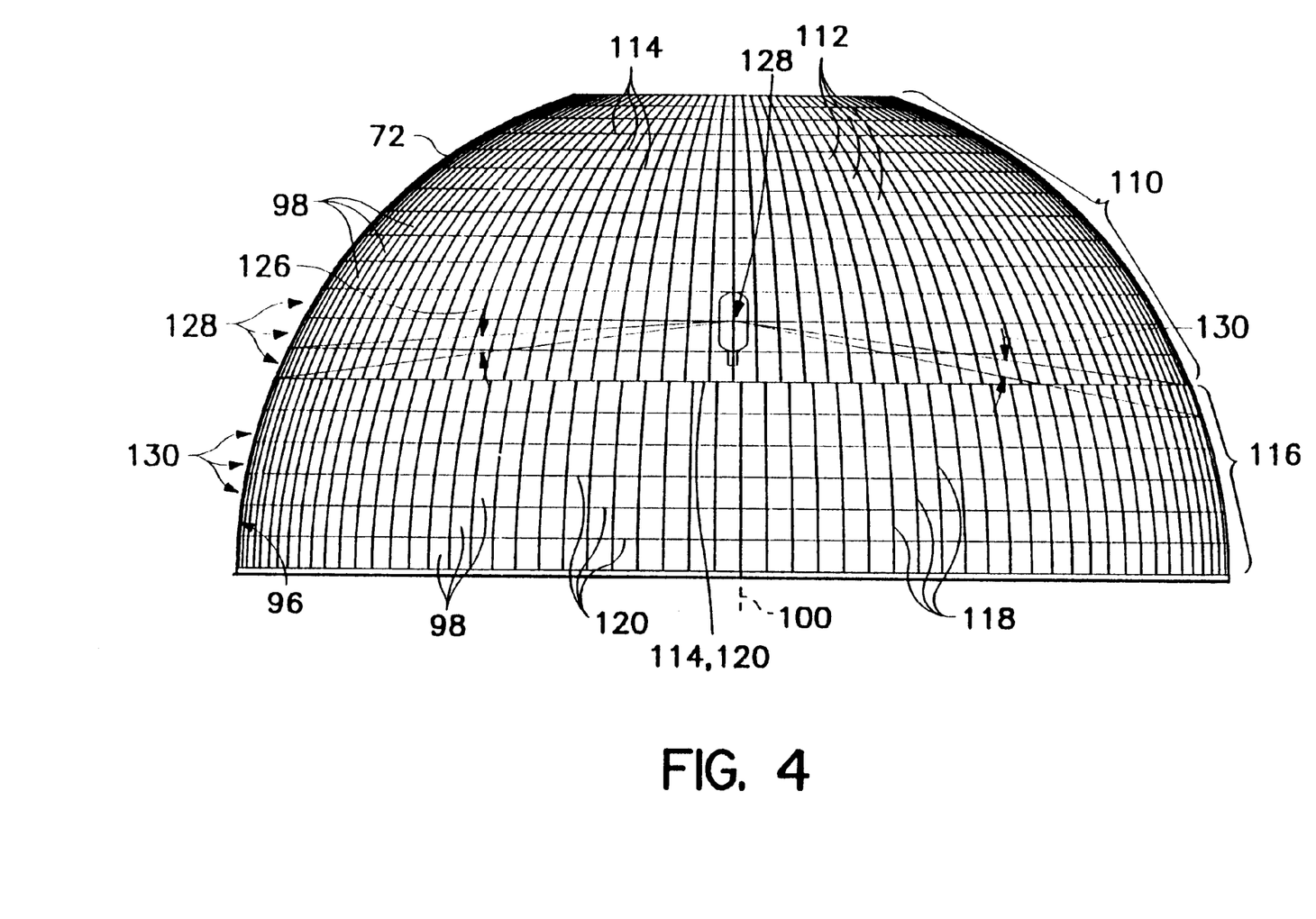
FIG. 4 is a sectional view of the reflector of FIG. 3, taken along line 4—4, showing that the latitudinal and longitudinal boundary lines associated with the first set of facets are angularly spaced from one another by a different amount than the latitudinal and longitudinal boundary lines associated with the second set of facets.

Lighthead 36 of surgical light apparatus 30 includes reflector 72 as previously described. Reflector 72 includes a concave reflector surface 96, shown for example in FIG. 2, that is formed to include a plurality of facets 98 as shown in FIGS. 3 and 4. In preferred embodiments, reflector 72 is made from a sheet of metal, such as aluminum, that is spun or otherwise formed into the desired shape and that is anodized, vacuum-metalized, or otherwise treated, if necessary, to provide concave reflector surface 96 with a mirror-like finish. Reflector 72 is somewhat dome-shaped and, therefore, has a central axis 100. Reflector 72 is shaped so that concave reflector surface 96 follows a generally elliptical curve and so that each facet 98 is substantially tangent to the elliptical curve. It is understood that a smooth surface defined by rotating an ellipse about an axis tends to focus light to a single point known as the focus of the ellipse. However, having a concentrated point of light on a patient during surgery is undesirable. By providing reflector 72 with facets 98, light reflected by reflector 72 is dispersed over a wider area than if concave reflector surface 96 were smooth, thereby avoiding the creation of a concentrated point of light.

Reflector 72 is formed so that facets 98 are separated into a first set 110 and a second set 116 as shown best in FIG. 4. Each facet 98 of first set 110 extends between respective longitudinal boundary lines 112 and respective latitudinal boundary lines 114 as shown in FIGS. 3 and 4. Likewise, each facet 98 of second set 116 extends between respective longitudinal boundary lines 118 and respective latitudinal boundary lines 120. Longitudinal boundary lines 112, 118 appear in FIG. 3 as lines that extend radially with respect to central axis 100 and latitudinal boundary lines 114, 120 appear in FIG. 3 as circles that are concentric with central axis 100. Of course, latitudinal boundary lines 114, 120 are not actually circles, but are comprised of a number of straight line segments which only appear in FIG. 3 to be circles because of the large number of such segments.

Because any circular, annular, or rotationally symmetric member, such as reflector 72, circumscribes three-hundred-sixty degrees, it is logical for adjacent longitudinal boundary lines 112, 118 to be separated by an angle that divides into 360 degrees evenly. Each longitudinal boundary line 112 is angularly spaced from each of the next adjacent longitudinal boundary lines 112 by an angle 122, which in preferred embodiments is four degrees, and each longitudinal boundary line 118 is angularly spaced from each of the next adjacent longitudinal boundary lines 118 by an angle 124, which in preferred embodiments is three degrees, as shown in FIG. 3. Thus, the angular spacing between longitudinal boundary lines 112 associated with the first set of facets 110 is different that the angular spacing between longitudinal boundary lines 118 associated with the second set of facets 116.

In preferred embodiments, reflector 72 is fabricated so that each latitudinal boundary line 114 is angularly spaced from each of the next adjacent latitudinal boundary lines 114 by an angle 126 with respect to a reference point 128 defined on main bulb 68 when main bulb 68 is in a nominal position between the lowermost and uppermost positions relative to reflector 72 and each latitudinal boundary line 120 is angularly spaced from each of the next adjacent latitudinal boundary lines 120 by an angle 130 with respect to reference point 128. In preferred embodiments, angle 126 is four degrees and angle 130 is three degrees. Thus, the angular spacing between latitudinal boundary lines 114 associated with the facets 98 of first set 110 is different that the angular spacing between latitudinal boundary lines 120 associated with the facets 98 of second set 116. In addition, angle 122 is substantially equivalent to angle 126 and angle 124 is substantially equivalent to angle 130.

In preferred embodiments, the first set 110 of facets 98 are arranged to provide reflector 72 with thirteen annular rows or upper courses, three courses of which are indicated in FIG. 4 by reference numeral 128, and the second set 116 of facets 98 are arranged to provide reflector 72 with six annular rows or lower courses 130, three courses of which are indicated in FIG. 4 by reference number 130. Each upper course 128 includes ninety facets 98 due to longitudinal boundary lines 112 being circumferentially spaced by four degrees from one another and each lower course 130 includes one-hundred-twenty facets 98 due to longitudinal boundary lines 114 being circumferentially spaced by three degrees from one another. A common latitudinal boundary line 114, 120, shown in FIGS. 3 and 4, exists at the boundary between upper courses 128 and lower courses 130.

Reflectors similar to reflector 72 but having facets with respective latitudinal and longitudinal boundary lines that are angularly spaced from one another in some other manner and having other numbers of upper and lower courses are within the scope of the invention as presently perceived. However, it has been found that the above-described geometry of concave reflector surface 96 results in a desired level of surgical site illumination performance for illustrative reflector 72, which, in preferred embodiments, has a lower peripheral opening 132 with a diameter of twenty-three inches.

One way of gauging the performance of a surgical light is to illuminate a reference surface that is perpendicular to the central axis of the associated surgical light and to measure and plot the luminous intensity on the reference surface as a function of the radial distance from the central axis. Plotting the luminous intensity in this way provides an illumination profile. A reference surface 133 perpendicular to central axis 100 is shown diagrammatically in FIG. 7.

Figure 5:
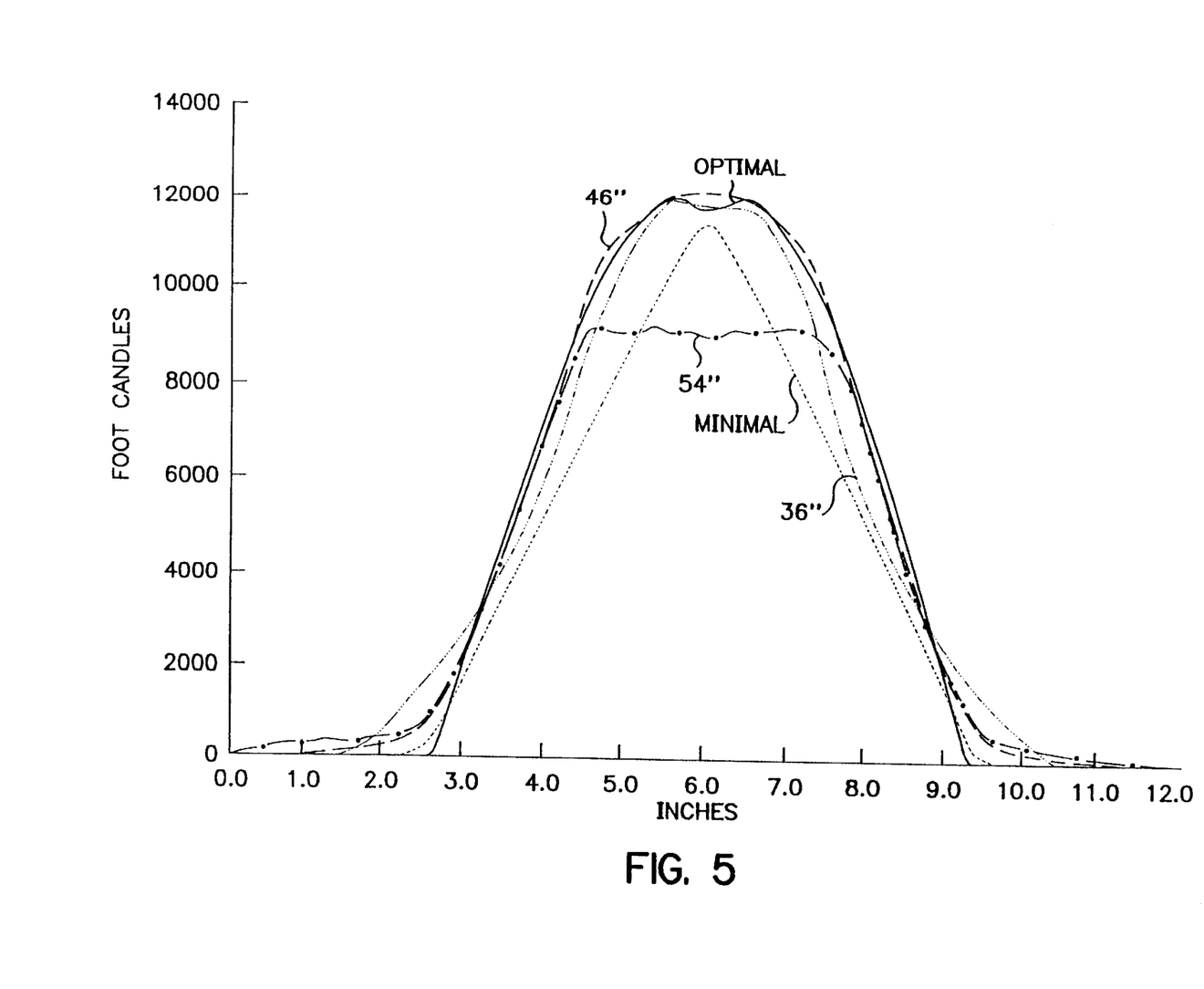
FIG. 5 is a graphical view of three illuminance profiles produced by the reflector of the first surgical lighthead along with minimal and optimal illuminance profiles showing the illumination performance of the first surgical lighthead at different distances from a reference surface illuminated by the surgical light.

FIG. 5 shows representative illumination profiles produced by reflector 72 at three different distances of surgical lighthead 36 from a corresponding reference surface, such as reference surface 133. FIG. 5 also shows an optimal illuminance profile and a minimal illuminance profile. In FIG. 5, central axis 100 of reflector 72 passes through the six inch gradation of the x-axis. The minimal illuminance profile represents an illuminance profile that avoids the appearance to an observer of dark rings around a bright center and the optimal illuminance profile represents an illuminance profile that, based on experience, provides a preferred light pattern with as few lumens as possible.

When surgical lighthead 36 is spaced apart from reference surface 133 by thirty-six inches and forty-six inches, the respective illuminance profiles produced by reflector 72 very closely approximate the optimal illuminance profile as shown in FIG. 5. When surgical lighthead 36 is spaced apart from reference surface 133 by fifty-four inches, a substantial portion of the illuminance profile produced by reflector 72 also closely approximates the optimal illuminance profile, although the peak luminous intensity is reduced in the central region of the fifty-four inch profile due to the large distance that separates surgical lighthead 36 from reference surface 133. As can be seen in FIG. 5, the pattern size of light produced by reflector 72 is substantially constant as surgical lighthead 36 is moved through a depth of field above reference surface 133 of thirty-six to fifty-four inches.

Figure 6:
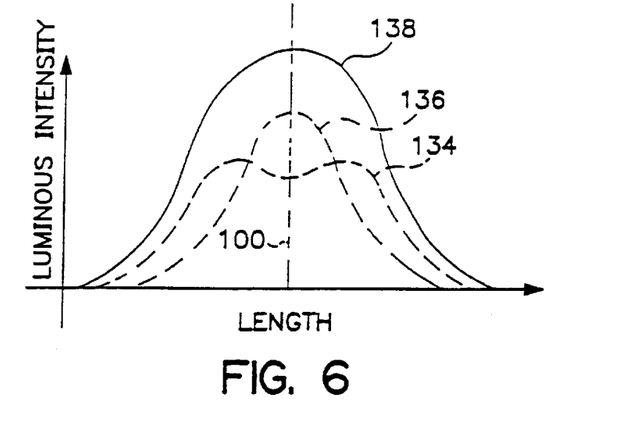
FIG. 6 is a graphical view showing a representative illuminance profile of the first surgical lighthead, a shadow performance portion of the illuminance profile produced by the lower set of facets, and a pattern size portion of the illuminance profile produced by the upper set of facets.

Reflector 72 includes first set 110 of facets 98 having upper courses 128 and a second set 116 of facets 98 having lower courses 130 as previously described. Upper and lower courses 128, 130 of facets 98 contribute differently to the overall illuminance profile of reflector 72. In general, upper courses 128 of facets 98 contribute predominantly to pattern size performance of surgical lighthead 36 and lower courses 130 of facets 98 contribute predominantly to shadow reduction performance of surgical lighthead 36. A diagrammatic graph in which a first profile 134 is representative of the illuminance profile generated by upper courses 128 of facets 98 and in which a second profile 136 is representative of the illuminance profile generated by lower courses 130, is shown in FIG. 6. First profile 134 cooperates with second profile 136 to produce an overall illuminance profile 138 of surgical lighthead 36.

In preferred embodiments, the location on concave reflector surface 96 of the latitudinal boundary line 114, 120, which provides the demarcation point between first set 110 and second set 116 of facets 98, is based upon a standard test, well-known to those skilled in the surgical light art as the IESNA Shadow Reduction Test. The IESNA Shadow Reduction test includes placing a ten inch diameter plate 140 twenty-nine inches above reference surface 133 over a standardized can 142 supported on reference surface 133, as shown diagrammatically in FIG. 7, and measuring the luminous intensity at a center 144 of the bottom of can 142 as a surgical lighthead to be tested is moved within a depth of field of thirty-eight to forty-eight inches above reference surface 133. Can 142 is three inches tall and has a diameter of two inches. Plate 140 and can 142 are each centered with respect to central axis 100 during the IESNA Shadow Reduction test.

Figure 7:
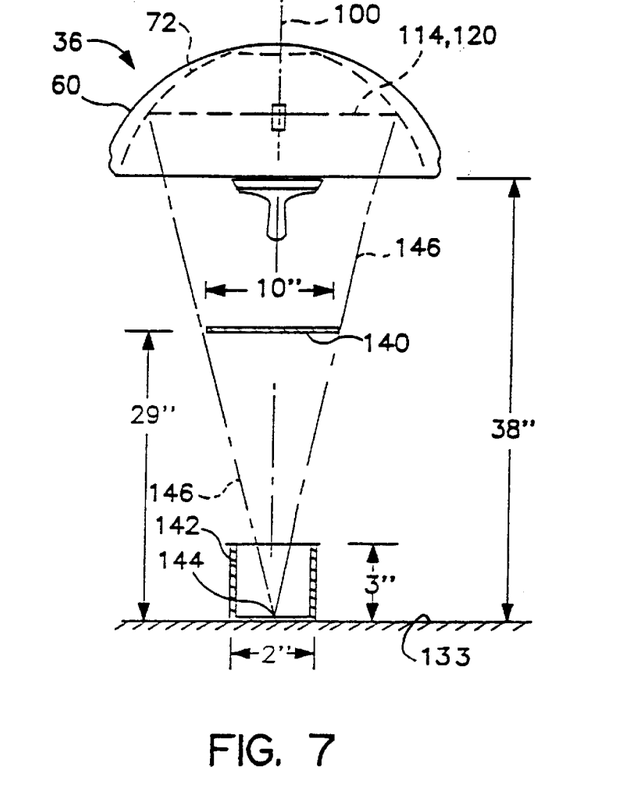
FIG. 7 is a diagrammatic view showing how a standard shadow reduction test is used to determine the location on the reflector of the boundary between the first and second sets of facets.

The location of latitudinal boundary line 114, 120 between sets 110, 116 of facets 98 is determined by projecting a cone 146, having its apex at center 144 of can 142, upwardly beyond the outer edge of plate 140 and onto concave reflector surface 96 when surgical lighthead 36 is at a position thirty-eight inches above reference surface 133 as shown in FIG. 7. Facets 98 associated with each course of lower courses 130 are arranged so as to direct light toward center 144 of can 142 when surgical lighthead 36 is positioned at incremental heights above reference surface 133. For example, facets 98 associated with the course 130 just beneath the latitudinal boundary line 114, 120 between sets 110, 116 of facets 98 are arranged to direct light toward center 144 of can 142 when surgical lighthead 36 is thirty-eight inches above reference surface 133 and the facets 98 associated with the lowermost course 130 just above lower peripheral opening 132 are arranged to direct light toward center 144 of can 142 when surgical lighthead 36 is forty-eight inches above reference surface 133. The facets 98 of each course of the remaining courses 130 are arranged to direct light toward center 144 of can 142 as surgical lighthead 36 is moved in two inch increments through the depth of field. Thus, the facets of the course 130 located just above the "forty-eight inch" course 130 are arranged to direct light toward center 144 of can 142 when lighthead 36 is forty-six inches above reference surface 133, the facets of the course 130 located just above the "forty-six inch" course 130 are arranged to direct light toward center 144 of can 142 when lighthead 36 is forty-four inches above reference surface 133, and so on.

By providing reflector 72 with sets 110, 116 of facets that contribute predominantly to different portions of the associated illuminance profile, reflector 72 produces a substantially constant pattern size over the depth of field of lighthead 36 while also producing acceptable shadow reduction performance. Some prior art surgical lights have smooth reflectors and lenses formed with a multiplicity of prisms that are configured to disperse light in a particular manner. See, for example, U.S. Pat. Nos. 5,485,319; 4,994,945; and 4,937,715. However, lenses having a multiplicity of prisms are relatively costly to manufacture as compared to the manufacturing costs of reflector 72 and have fresnel refraction losses that exceed those associated with reflector 72 of the present invention.

Although the invention has been described in detail with reference to a certain preferred embodiment, variations and modifications exist within the scope and spirit of the invention as described and as defined in the following claims.

What is claimed is:

1. A surgical lighthead comprising
   a light source having a reference point defined thereon, and
   a reflector including a concave reflector surface having a central axis, the concave reflector surface being formed to include a plurality of facets configured to reflect light emanating from the light source, each facet extending between an associated pair of longitudinal boundary lines and an associated pair of latitudinal boundary lines, the latitudinal boundary lines defining a first plurality of planes, the central axis being perpendicular to each of the first plurality of planes, the longitudinal boundary lines defining a second plurality of planes, the central axis lying on each of the second plurality of planes, the plurality of facets including a first set of facets for which each associated longitudinal boundary line is angularly spaced by a first angle from each of the next adjacent longitudinal boundary lines relative to the central axis, the first set of facets defining at least two annular courses of facets, and the plurality of facets including a second set of facets for which each associated longitudinal boundary line is angularly spaced by a second angle from each of the next adjacent longitudinal boundary lines relative to the central axis.

2. The surgical lighthead of claim 1, wherein each latitudinal boundary line associated with the first set of facets is angularly spaced by a third angle from each of the next adjacent boundary lines relative to the reference point and each latitudinal boundary line associated with the second set of facets is angularly spaced by a fourth angle from each of the next adjacent boundary lines relative to the reference point.

3. The surgical lighthead of claim 2, wherein the first angle is substantially equivalent to the third angle and the second angle is substantially equivalent to the fourth angle.

4. The surgical lighthead of claim 3, wherein the first and third angles are each about three degrees and the second and fourth angles are each about four degrees.

5. The surgical lighthead of claim 2, wherein the first set of facets define a first number of annular courses of facets and the second set of facets define a second number of annular courses of facets.

6. The surgical lighthead of claim 5, wherein the second number is at least twice the first number.

7. The surgical lighthead of claim 1, wherein the reflector cooperates with the light source to illuminate a reference surface perpendicular to the central axis, the illumination of the reference surface is characterized by an illuminance profile, the first set of facets reflects light that contributes primarily to a shadow reduction performance portion of the illuminance profile, and the second set of facets reflects light that contributes primarily to a pattern size portion of the illuminance profile.

8. The surgical lighthead of claim 1, wherein the central axis of the reflector extends through the reference point of the light source.

9. The surgical lighthead of claim 1, wherein the concave reflector surface is defined by a portion of an ellipse rotated about the central axis and each facet of the plurality of facets is tangent to the portion of the ellipse.

10. The surgical lighthead of claim 9, wherein the reference point is coincident with a focus of the ellipse.

11. The surgical lighthead of claim 1, further comprising a light absorption filter surrounding the light source so that light emanating from the light source passes through the light absorption filter before reaching the reflector.

12. The surgical lighthead of claim 11, wherein the reflector includes a main opening through which light reflected from the reflector passes and further comprising a lens covering the main opening and having substantially planar inner and outer surfaces that are each substantially perpendicular to the central axis.

13. The surgical lighthead of claim 1, wherein the reflector includes a main opening through which light reflected from the reflector passes and further comprising a lens covering the main opening and having substantially planar inner and outer surfaces that are each substantially perpendicular to the central axis.

14. A surgical lighthead comprising
    a light source having a reference point defined thereon, and
    a reflector including a concave reflector surface having a central vertical axis, the concave reflector surface being formed to include a plurality of facets configured to reflect light emanating from the light source, the plurality of facets including a first set of facets which each extend between an associated pair of first longitudinal boundary lines and an associated pair of first latitudinal boundary lines, the plurality of facets including a second set of facets which each extend between an associated pair of second longitudinal boundary lines and an associated pair of second latitudinal boundary lines, the first latitudinal boundary lines being angularly spaced relative to the reference point by a different amount than the second latitudinal boundary lines are angularly spaced relative to the reference point, the first and second latitudinal boundary lines defining a first plurality of planes, the central axis being perpendicular to each of the first plurality of planes, the first and second longitudinal boundary lines defining a second plurality of planes, the central axis lying on each of the second plurality of planes.

15. The surgical lighthead of claim 14, wherein the first longitudinal boundary lines are angularly spaced relative to the central axis by a different amount than the second longitudinal boundary lines are angularly spaced relative to the central axis.

16. The surgical lighthead of claim 14, wherein the reflector cooperates with the light source to illuminate a reference surface perpendicular to the central axis, the illumination of the reference surface is characterized by an illuminance profile, the first set of facets reflects light that contributes primarily to a shadow performance portion of the illuminance profile, and the second set of facets reflects light that contributes primarily to a pattern size portion of the illuminance profile.

17. The surgical lighthead of claim 14, wherein the concave reflector surface is defined by a portion of an ellipse rotated about the central axis and each facet of the plurality of facets is tangent to the portion of the ellipse.

18. The surgical lighthead of claim 17, wherein the reference point is coincident with a focus of the ellipse.

19. The surgical lighthead of claim 14, wherein the reflector includes a main opening through which light reflected from the reflector passes and further comprising a lens covering the main opening and having substantially planar inner and outer surfaces that are each substantially perpendicular to the central axis.

20. A surgical lighthead comprising
a light source,
a reflector including a concave reflector surface formed to include a plurality of facets configured to reflect light emanating from the light source, the plurality of facets including a first set of facets arranged to contribute primarily to shadow reduction performance of the surgical lighthead, and the plurality of facets including a second set of facets arranged to contribute primarily to pattern size performance of the surgical lighthead such that the first and second sets of facets contribute primarily differently to the performance of the surgical lighthead.

21. The surgical lighthead of claim 20, wherein the reflector cooperates with the light source to illuminate a reference surface, the illumination of the reference surface is characterized by an illuminance profile, and the plurality of facets are further configured such that the illuminance profile remains generally consistent as the surgical lighthead is moved between a first position thirty-eight inches from the reference surface and a second position fifty-four inches from the reference surface.

22. The surgical lighthead of claim 20, wherein a reference point is defined on the light source, each of the facets of the first set of facets extends between an associated pair of first longitudinal boundary lines and an associated pair of first latitudinal boundary lines, each of the facets of the second set of facets extends between an associated pair of second longitudinal boundary lines and an associated pair of second latitudinal boundary lines, the first latitudinal boundary lines being angularly spaced relative to the reference point by a different amount than the second latitudinal boundary lines are angularly spaced relative to the reference point.

23. The surgical lighthead of claim 20, wherein the concave reflector surface defines a central axis, each of the facets of the first set of facets extends between an associated pair of first longitudinal boundary lines and an associated pair of first latitudinal boundary lines, each of the facets of the second set of facets extends between an associated pair of second longitudinal boundary lines and an associated pair of second latitudinal boundary lines, and the first longitudinal boundary lines are angularly spaced relative to the central axis by a different amount than the second longitudinal boundary lines are angularly spaced relative to the central axis.

24. A surgical lighthead comprising
a light source,
a light absorption filter surrounding the light source, the light absorption filter being configured to absorb a portion of infrared light passing therethrough,
a reflector including a concave reflector surface formed to include a plurality of facets configured to reflect light emanating from the light source, the plurality of facets including a first set of facets arranged to contribute primarily to shadow reduction performance of the surgical lighthead, and the plurality of facets including a second set of facets arranged to contribute primarily to pattern size performance of the surgical lighthead such that the first and second sets offacets contribute primarily differently to the performance of the surgical lighthead, the reflector having a main opening through which light reflected from the reflector passes, and
a lens covering the main opening so that light reflected from the facets of the concave reflector surface passes through the lens.

25. The surgical lighthead of claim 24, wherein a reference point is defined on the light source, the plurality of facets includes a first set of facets which each extend between an associated pair of first longitudinal boundary lines and an associated pair of first latitudinal boundary lines, the plurality of facets includes a second set of facets which each extend between an associated pair of second longitudinal boundary lines and an associated pair of second latitudinal boundary lines, and the first latitudinal boundary lines are angularly spaced relative to the reference point by a different amount than the second latitudinal boundary lines are angularly spaced relative to the reference point.

26. The surgical lighthead of claim 24, wherein the concave reflector surface defines a central axis, the plurality of facets includes a first set of facets which each extend between an associated pair of first longitudinal boundary lines and an associated pair of first latitudinal boundary lines, the plurality of facets includes a second set of facets which each extend between an associated pair of second longitudinal boundary lines and an associated pair of second latitudinal boundary lines, and the first longitudinal boundary lines are angularly spaced relative to the central axis by a different amount than the second longitudinal boundary lines are angularly spaced relative to the central axis.

* * * * *